(12) United States Patent
Li

(10) Patent No.: US 11,298,439 B2
(45) Date of Patent: *Apr. 12, 2022

(54) ELECTRONIC SCENT PRODUCING IMITATION CANDLE DEVICE

(71) Applicant: L&L Candle Company, LLC, Brea, CA (US)

(72) Inventor: Xiaofeng Li, Shenzhen (CN)

(73) Assignee: L&L Candle Company, LLC, Brea, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 16/518,060

(22) Filed: Jul. 22, 2019

(65) Prior Publication Data

US 2020/0179552 A1 Jun. 11, 2020

Related U.S. Application Data

(63) Continuation of application No. 15/908,718, filed on Feb. 28, 2018, now Pat. No. 10,357,587.

(30) Foreign Application Priority Data

May 26, 2017 (CN) .......................... 201710387091.2

(51) Int. Cl.
*A61L 9/03* (2006.01)
*F21S 10/04* (2006.01)
(Continued)

(52) U.S. Cl.
CPC ................. *A61L 9/03* (2013.01); *A61L 9/032* (2013.01); *A61L 9/035* (2013.01); *F21S 10/046* (2013.01);
(Continued)

(58) Field of Classification Search
CPC ......... G08C 2201/20; H01H 2231/032; H01H 9/0235; H01R 13/665; H01R 13/7038;
(Continued)

(56) References Cited

U.S. PATENT DOCUMENTS 4,191,868 A * 3/1980 Sunde ..................... F16K 17/36
200/61.5
5,843,284 A 12/1998 Waters et al.
(Continued)

*Primary Examiner* — Tu B Hoang
*Assistant Examiner* — Vy T Nguyen
(74) *Attorney, Agent, or Firm* — Perkins Coie LLP

(57) ABSTRACT

Electronic imitation candle devices are described that produce a scent while including a flame-like element that simulates a real fire flame. One example device includes a support assembly having a base, a top plate and a support rod that connects the base and the top plate, as well as a flame element and a light source to simulate a real candle flame. The device also includes a fragrance compartment above the top plate that includes a lid removably positioned on top of the fragrance container. The device is further provided with a heating element above the top plate and below the fragrance container to provide heat to the fragrance container, and a switch coupled to the lid of the fragrance container and operable to sense that the fragrance container is covered by the lid and to deactivate the heating element when the fragrance container is covered by the lid.

20 Claims, 10 Drawing Sheets

(51) Int. Cl.
*H05B 47/11* (2020.01)
*F21W 121/00* (2006.01)

(52) U.S. Cl.
CPC ............ *H05B 47/11* (2020.01); *A61L 2209/11* (2013.01); *A61L 2209/111* (2013.01); *A61L 2209/12* (2013.01); *F21W 2121/00* (2013.01)

(58) Field of Classification Search
CPC ... H01R 13/72; H01R 25/003; Y10T 307/461; Y10T 307/492; Y10T 307/766; B06B 1/0238; A01M 29/12; A01M 1/205; A61L 9/14; A61L 9/127; A61L 2209/132; A61L 2209/12; B05B 17/0684; B05B 17/0646; B05B 17/0607; F21Y 2101/00; F21W 2121/00; F21S 10/04; F21S 6/001; F21V 23/04
See application file for complete search history.

(56) References Cited

U.S. PATENT DOCUMENTS

| | | | | |
|---|---|---|---|---|
| 7,046,919 | B2* | 5/2006 | Shimizu | A61L 9/03 392/390 |
| 9,655,168 | B2* | 5/2017 | Belongia | H05B 3/26 |
| 2002/0101220 | A1* | 8/2002 | Yang | H04N 7/104 320/150 |
| 2003/0082494 | A1 | 5/2003 | Campbell | |
| 2005/0074358 | A1* | 4/2005 | Hart | A61L 9/048 422/5 |
| 2007/0115653 | A1 | 5/2007 | Cea et al. | |
| 2008/0169354 | A1* | 7/2008 | Bankers | A61L 9/127 239/6 |
| 2010/0096376 | A1* | 4/2010 | Hsiao | A61L 9/03 219/201 |
| 2010/0270943 | A1* | 10/2010 | Cook | G09F 23/04 315/291 |
| 2011/0110072 | A1* | 5/2011 | Hsiao | A61L 9/03 362/96 |
| 2011/0110118 | A1* | 5/2011 | Hsiao | F21V 33/0004 362/643 |
| 2012/0024837 | A1* | 2/2012 | Thompson | A61L 9/03 219/433 |
| 2012/0093491 | A1 | 4/2012 | Browder et al. | |
| 2012/0104197 | A1 | 5/2012 | Jensen | |
| 2012/0318779 | A1* | 12/2012 | Juarez | H05B 3/06 219/209 |
| 2013/0020307 | A1 | 1/2013 | Ashton et al. | |
| 2013/0216673 | A1 | 8/2013 | Storek et al. | |
| 2014/0133131 | A1 | 5/2014 | Hsiao | |
| 2014/0140042 | A1 | 5/2014 | Schreiber | |
| 2015/0061901 | A1* | 3/2015 | Casparian | H01H 13/705 341/22 |
| 2015/0108243 | A1* | 4/2015 | Bourne | A61L 9/125 239/58 |
| 2016/0130050 | A1 | 5/2016 | St. Clair | |
| 2018/0052496 | A1 | 2/2018 | Tucker et al. | |

* cited by examiner

ELECTRONIC SCENT PRODUCING IMITATION CANDLE DEVICE

RELATED APPLICATIONS

This patent document is a continuation of U.S. patent application Ser. No. 15/908,718, filed Feb. 28, 2018, which claims priority to Chinese Patent Application No. 201710387091.2, filed May 27, 2017. The entire contents of the before mentioned patent applications are incorporated by reference in this patent document.

FIELD OF THE INVENTION

The subject matter of this patent document relates to devices and techniques that produce an aromatic scent, and in particular to devices and techniques that produce light in addition to aroma.

BACKGROUND

The first appearance of aroma producing devices dates back to the Han Dynasty and the Warring States Period and their use persist even to present day. In early scent producing imitation candle device s, an aroma stove is placed on a level surface, water is added into a recess on the top of the devices, 3 to 5 drops of pure essential oil are then added, and then a tealight is placed into an opening at the bottom of the essential oil stove. When the tealight is lit, the water temperature at the top slowly increases, and a scent is slowly dispersed into the air along with some steam as the water is evaporated. The scent is diminished and is ultimately gone when the tealight is extinguished. Such an aroma stove provides several tangible features such as masking odors, and purifying the air, as well as supposed benefits including refreshing the brain, clearing the mind and improving work efficiency. But the traditional aroma stove has the following drawbacks: first, the aroma stove has a high surface temperature that can cause burns and injuries, especially, to children and pets. Second, the candle has an open flame which can lead to fires. Third, an essential oil must be repeatedly added into the recess, which makes the stove difficult to clean. Over the recent years, scent producing imitation candle device s have been developed that include a light bulb to heat an essential oil, and melt the wax in the recess through the heat of the bulb itself. However, the bulb can only emit light, and does not flicker like a candle, and thus it does not and cannot create a romantic environment. In addition, the bulb is too hot, which leads to a very high surface temperature. As a result, similar to the traditional aroma stove, it can lead to injury and burns to adults, children and pets.

SUMMARY OF CERTAIN EMBODIMENTS

One aspect of the disclosed embodiments related to an electronic scent producing imitation candle device that includes a support assembly comprising a base, a support rod and a top plate, where the support rod connects the base and the top plate. The device further includes a flame element and a light source for illuminating the flame element to simulate a real flame, where the flame element and the light source are positioned the base and below the top lid. The device further includes a fragrance compartment positioned above the top plate; the fragrance container includes a lid that can be removably positioned on top of the fragrance container to cover the fragrance compartment. The device additionally includes a heating element positioned above the top plate and below the fragrance container to provide heat to the fragrance container, and a switch coupled to the lid of the fragrance container and operable to sense whether or not the lid is positioned to cover the fragrance container and to deactivate the heating element upon sensing that the fragrance container is covered by the lid.

In one embodiment, the switch is mechanically coupled to the lid to sense a downward or an upward movement of the lid. In another embodiment, the switch is configured to deactivate the heating element upon detection of a downward movement of the lid and to activate the heating element upon detection of an upward movement of the lid. In yet another embodiment, the device further includes an insulation lid positioned under the lid to impede transfer of heat to the lid. According to still another embodiment, the lid includes a hollow structure that protrudes downward from a center of the fragrance compartment; the hollow structure includes an elastic material therein that allows the lid to be pressed downward or to moved upward.

According to another embodiment, the electronic scent producing imitation candle device further includes a locking base positioned within the device below the fragrance compartment to lock in place the lid when the lid is moved downward. In one embodiment, the fragrance compartment includes one or more partitions that divide the fragrance container into a plurality of chambers. In one example, each chamber is configured to hold a particular fragrance material that is different from fragrance materials in other chambers. In yet another example, the plurality of chambers are in communication with each other to enable scents from a variety of fragrances to be mixed in the fragrance compartment.

In yet another embodiment, the electronic scent producing imitation candle device includes an indicator light positioned to illuminate the fragrance compartment with light. For example, the indicator light can be configured to illuminate the fragrance container with any one of a plurality of colored lights. In particular, a first colored light is indicative of a low temperature of the fragrance compartment, a second colored light is indicative of a medium temperature of the fragrance compartment and a third colored light is indicative of a high temperature of the fragrance compartment. According to another embodiment, at least a section of the fragrance compartment is made of a clear material or a translucent material to allow contents of the fragrance compartment to be viewed.

In another embodiment, the electronic scent producing imitation candle device further includes a power cord to deliver power to the electronic scent producing imitation candle device, a remote control device that allows control of the operations of the electronic scent producing imitation candle device from a remote location, and a control panel coupled to the power cord. The control panel includes a plurality of buttons that allow control of an operation of the electronic scent producing imitation candle device. In one example embodiment, each of the remote control device and the control panel includes a corresponding magnetic element thereon; the remote control device is configured to be mounted on the control panel at least in-part due to attractive forces of magnets on the remote control device and the control panel. In another example embodiment, the remote control device includes a clearance groove configured to prevent the remote control device from contacting the buttons on the control panel when the remote control device is mounted on top of the control panel. According to one exemplary embodiment, the remote control device and the control panel include mutually matching structures that enable installation of the remote control device onto the control panel.

In another embodiment, the top plate of the support assembly includes an installation groove for accommodating placement of the fragrance compartment inside the installation groove. In yet another embodiment, the electronic scent producing imitation candle device also includes a temperature control device to control an on/off operation of the heating element according to a temperature of a fragrance material inside the fragrance compartment. In still another embodiment, the device further comprises a shell disposed along a periphery of the support assembly; the shell includes an observation window thereon to allow the flame element to be viewed from outside of the electronic scent producing imitation candle device. In another exemplary embodiment, the device further includes an electromagnet coupled to the lid and configured to close or open the lid in response to activation of the electromagnet.

According to another embodiment, the electronic scent producing imitation candle device further includes a sensor positioned to detect a presence or absence of a fragrance material within the fragrance compartment, and to affect a supply of power to the heating element in response thereto. In one embodiment, the sensor is configured to (a) deactivate the supply of power to the heating element upon detection of an empty fragrance compartment or a presence of a nominal amount of fragrance in the fragrance compartment, and (b) reactivate the supply of power to the heating element upon detection of a presence of fragrance compartment beyond the nominal amount. In one embodiment, the sensor is configured to activate or deactivate in response to a weight of the fragrance compartment.

BRIEF DESCRIPTION OF THE DRAWINGS

FIG. 3b illustrates an exploded view of the electronic scent producing imitation candle device shown in FIG. 3a.

DETAILED DESCRIPTION OF THE INVENTION

In this patent document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Figure 1:
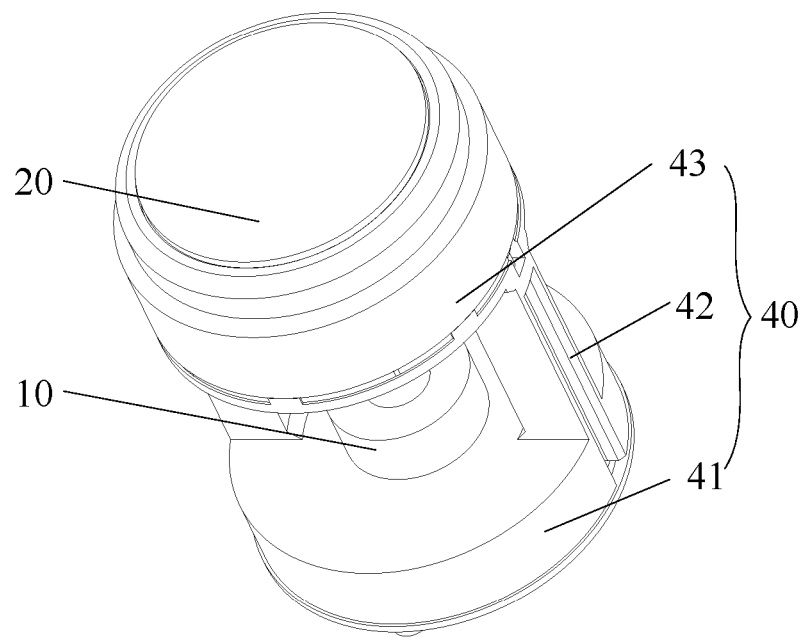
FIG. 1 illustrates an electronic scent producing imitation candle device according to an exemplary embodiment.

As shown in FIG. 1, an electronic scent producing imitation candle device according to an exemplary embodiment that comprises a support assembly 40, a flame simulation device 10, and a fragrance compartment or container 20. The support assembly 40 comprises a base 41, a support rod 42, and a top plate 43, where one end of the support rod 42 is connected to the base 41 and another end of the support rod 42 is connected to the top plate 43, respectively. The top plate 43 is positioned above the base 41, and the flame simulation device 10 is disposed on the base 41. The flame simulation device 10 is constructed to simulate a real fire flame. The fragrance compartment or container 20 is disposed on the top plate 43, and the fragrance compartment or container 20 is constructed to contain a fragrance.

According to the above embodiment, a fragrance is added into the fragrance compartment or container 20, and the fragrance in the fragrance compartment or container 20 is slowly evaporated into the air. The flame simulation device 10 simulates a flickering flame, such that the electronic scent producing imitation candle device simulates an aroma stove that disseminates an aroma using what appears to be a real candle. Compared to existing scent producing imitation candle devices, the flame simulation device 10 simulates a real flame, emits light and flickers like a real flame, and can create a romantic atmosphere; at the same time, it avoids potential risks of a real fire and associated burns and hazard that are caused by an open flame.

In some embodiments, the electronic scent producing imitation candle device comprises: a heating element 30, and the heating element 30 is disposed below the fragrance compartment or container 20, and is configured to heat the fragrance compartment or container 20 (see, e.g., FIG. 4).

In such embodiments, after a fragrance is added into the fragrance compartment or container 20, the heating element 30 heats the fragrance compartment or container 20, and the fragrance in the fragrance compartment or container 20 is slowly evaporated into the air. At the same time, the flame simulation device 10 simulates a flickering real flame. Such a device not only simulates a real flickering flame, but it also disseminates an aroma, and at the same time, it avoids potential risks associated with an open fire flame. In the embodiments that use a hearing element 30, the heating element 30 heats the fragrance compartment or container 20. Since the temperature of the heating element 30 is controllable, the temperature that the temperature of the fragrance compartment or container 20 can be controlled within a desired range that is tolerable to the human body, thus eliminating the problems that are associated with devices that are heated by an open flame or a bulb. It should be noted that the fragrance may be either a liquid fragrance or a solid fragrance.

Figure 2:
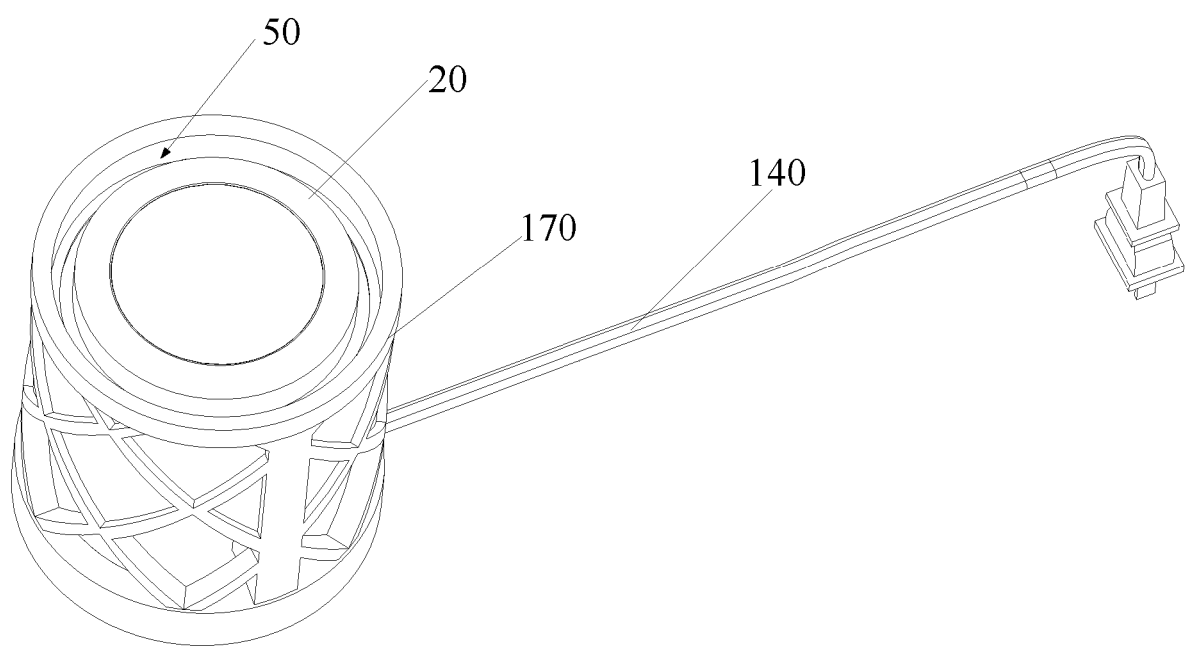
FIG. 2 illustrates an electronic scent producing imitation candle device according to another exemplary embodiment.
Figure 3A:
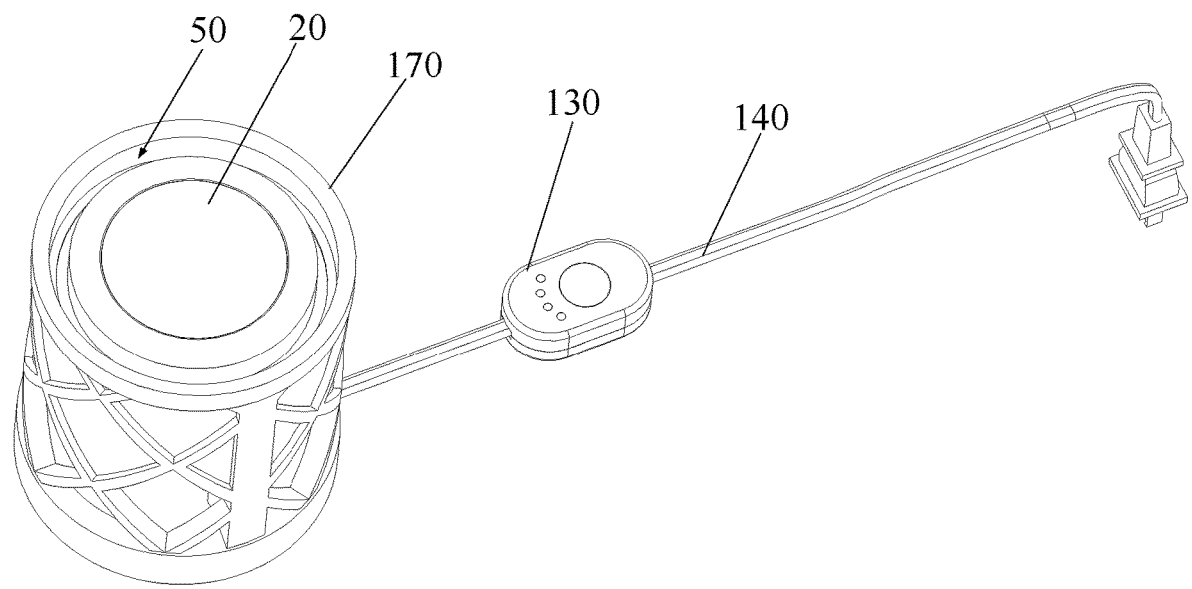
FIG. 3a illustrates an electronic scent producing imitation candle device according to yet another exemplary embodiment.
Figure 3B:
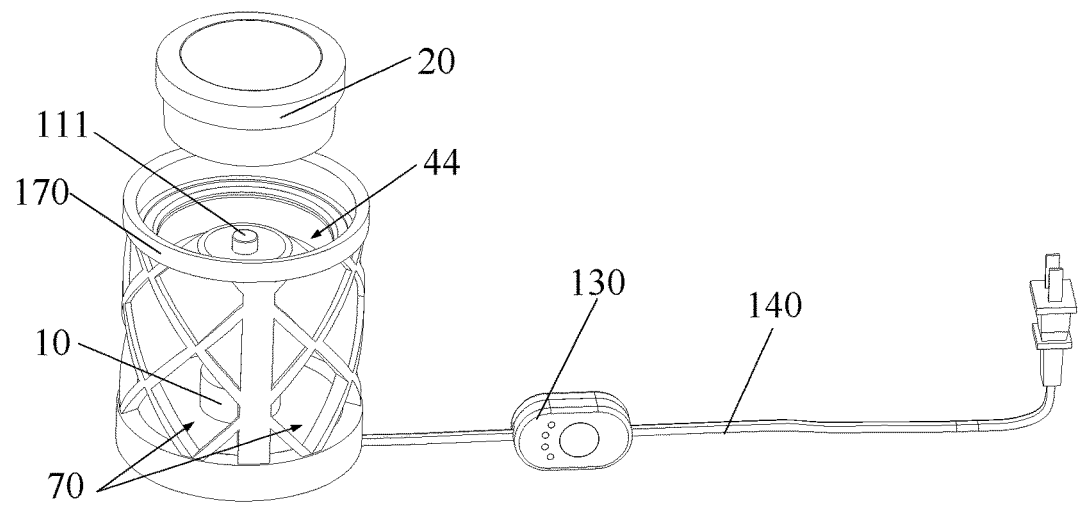

In some embodiments, as shown, for example, in FIGS. 2 through 3b, a gap exists between the heating element 30 and the flame simulation device 10, which facilitates heat dissipation for the heating element 30. In one embodiment, one heating element 30 may be provided, and in other embodiments, a plurality of heating elements 30 may be provided. One or a plurality of flame simulation devices 10 may be provided. Numbers of the heating elements 30 and the flame simulation devices 10 may be determined by a person skilled in the art according to specific needs or applications. For example, the electronic scent producing imitation candle device can include one heating element 30 and three flame simulation devices 10, or three heating elements 30 and one flame simulation device 10.

In some embodiments, the electronic scent producing imitation candle device further comprises a fan to blow air into the fragrance compartment or container 20 to accelerate the evaporation rate of the fragrance. The heating element 30 and the fan may operate simultaneously to enable the fragrance to be rapidly volatilized into the air, and to allow the scent to quickly disperse through an indoor environment. After operating the device for a predetermined period of time, one of the heating elements 30 and/or the fan can be turned off to allow the fragrance to slowly vaporize and thus control the rate of aroma dissipation.

In some embodiments, as shown, for example, in FIGS. 2 through 3b, the electronic scent producing imitation candle device comprises a shell 170 disposed along the periphery of the support assembly 40. The shell 170 may be made of any one of the materials including wax, resin, ceramic, iron pieces, plastics, crystal, glass, wood, or any combination thereof. In another embodiment, the shell 170 may be include a transparent material, a translucent material or an opaque material so as to allow the flickering or swaying imitation flame to be visible through a transparent or translucent shell. Referring to FIGS. 2 to 3b, the shell 170 is preferably constructed to have a cylindrical shape. In some embodiments, however, the shell 170 can have a cross section having a triangular, a square, an oval, or an irregular shape. In one embodiment, an insulation layer 60 (see, e.g., FIGS. 5 and 7) is disposed between the heating element 30 and the shell 170 to prevent the heat of the heating element 30 from being transferred to the shell 170, thereby ensuring that the temperature of the shell 170 is maintained at a low enough temperature which avoids burns or other injuries. In one exemplary embodiment, the insulation layer 60 includes a silica gel insulation layer.

In some embodiments, as shown, for example, in FIG. 3b, the top plate 43 is provided with an installation groove 44, and the fragrance compartment or container 20 is disposed inside the installation groove 44. The installation groove 44 limits the depth at which the fragrance compartment or container 20 can installed, and ensures the stability of the fragrance compartment or container 20 during use. In one embodiment, a space 50 (see, e.g., FIG. 3a) is provided between an external side wall of the fragrance compartment or container 20 and a side wall of the installation groove 44. The space 50 allows the fragrance compartment or container 20 to be taken out of the installation groove 44 by enabling a user to extend his/her fingers into the space 50, and remove the fragrance compartment or container 20. In one embodiment, a top surface of the fragrance compartment or container 20 is higher than a top surface of the top plate 43. In this embodiment, a user can directly grab the portion of the fragrance compartment or container 20 that sits higher than the top plate 43 to adjust the position of the fragrance compartment or container 20, to rotate or to move the same. This feature additionally allows the user to directly grab and remove the fragrance compartment or container 20, if needed.

In some embodiments, as shown, for example, in FIGS. 2 to 3b, the shell 170 is provided with an observation window 70 thereon to allow observation of the flame simulation device 10, and the associated simulated flame. The observation window 70 can include a hole with a specific shape, such as a rectangle, a rhombus, an ellipse, a petal shape or a combination thereof. As shown in exemplary diagrams of FIGS. 2 to 3b, the shell 170 can have a cylindrical shape, having an external surface that includes alternately arranged projections that form a plurality of rhombus shaped windows on the external surface of the shell 170. At least one the rhombus-shaped features is hollow and can be used as the observation window 70.

In some embodiments, as shown in, for example, FIGS. 4 to 10c, the fragrance compartment or container 20 comprises a compartment body 21 and a compartment lid 22. The compartment body 21 is constructed to hold a fragrance, and the compartment lid 22 is constructed to cover the compartment body 21. In some embodiments, the compartment lid 22 can be fully or partially removed from the compartment body 21. Such a compartment lid 22 prevents evaporation of the fragrance material in the fragrance compartment or container 20 when the device is not in use, thereby extending the useful life of the fragrance material. In addition, the compartment lid prevents foreign objects to fall into the fragrance. In some embodiments, as shown, for example, in FIGS. 4 to 10c, the fragrance compartment or container 20 further comprises an insulation lid 23 that covers the box body 1. In the exemplary illustrations, the insulation lid 23 is ring-shaped, and the compartment lid 22 covers the insulation lid 23. When the heating element 30 heats the fragrance compartment or container 20, the heat on the compartment body 21 cannot be transferred to the compartment lid 22 due to the presence of the insulation lid 23 between the compartment lid 22 and the compartment body 21. As such, the temperature of the compartment lid 22 does not reach a high temperature thus preventing potential burns or injuries to the users. In a preferred embodiment, the insulation lid 23 is a curved lid, and the curved insulation lid 23 can reflect the heat waves back into the fragrance compartment or container 20, further reducing the heat that is transferred through the insulation lid 23. Moreover, the insulation lid 23 and the compartment body 21 can be formed as separate structures; such a separation is manifested as a gap between the insulation lid 23 and the compartment body 21. In this implementation, the heat from the compartment body 21 needs to pass through the air in the gap before reaching the insulation lid 23. Since air is a poor conductor of heat, the heat from the compartment body 21 cannot be readily transferred to the compartment lid 22. Thus, the temperature of the compartment lid 22 is further maintained at a low temperature. In some embodiments, however, the compartment body 21 and the insulation lid 23 may also have an integral structure.

In some embodiments, a part or all sections of the fragrance compartment or container 20 is made of a clear material or a translucent material. A user can observe, through the fragrance compartment or container 20, the quantity of the fragrance therein, which allows the user to replenish the promptly fragrance as needed. For example, the compartment lid 22 can be made of a clear material, and a user can observe, through the compartment lid 22, the quantity of the fragrance therein. In another example, the fragrance compartment or container 20 includes a window, and a user can observe, through the window, the quantity of the fragrance in the fragrance compartment or container 20. In some embodiments, the compartment body 21 includes a scale, a reticle, measurement marks, etc., which allow the user to observe the quantity of fragrance remaining in the fragrance compartment or container 20. The fragrance compartment or container 20 may be constructed to have a variety of shapes, including, but not limited to, cylindrical, flower-shaped, flame-shaped or star-shaped.

In some embodiments, as shown in, for example, FIGS. 7, and 10a through 10c, the electronic scent producing imitation candle device further comprises an indicator 80 disposed between the fragrance compartment or container 20 and the top plate 43 that illuminates the fragrance compartment or container 20. In some embodiments, the fragrance compartment or container 20 is made of a clear material or a translucent material, and the indicator 80 can illuminate the fragrance compartment or container 20 with a particular color. For example, the indicator 80 can change colors (e.g., from red, blue and green colors), thus illuminating the fragrance container with different color. These features not only enhance the aesthetic qualities of the device, but they also allow the candle device to be easily identified (e.g., in a dark place). In some embodiments, the color of the indicator 80 varies in correspondence with the temperature of the fragrance compartment or container 20. For example, when the temperature of the fragrance compartment or container 20 increases, the indicator 80 gradually changes from white to red so as to let the user know that the temperature of the fragrance compartment or container 20 is too high. In some embodiments, a plurality of indicators 80 are provided, which can be disposed at different positions to illuminate the fragrance compartment or container 20. The plurality of indicators 80 may have the same color, or may have different colors. During the operation, the plurality of indicators 80 may light up simultaneously or individually to illuminate the fragrance compartment or container 20. In some implementations, the indicator 80 includes an LED.

Figure 11A:
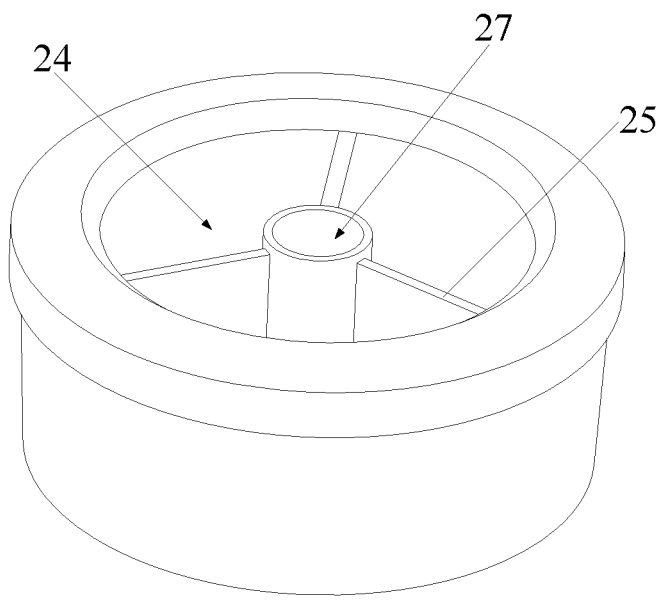
FIG. 11a illustrates a diagram of a fragrance container according to an exemplary embodiment.
Figure 11B:
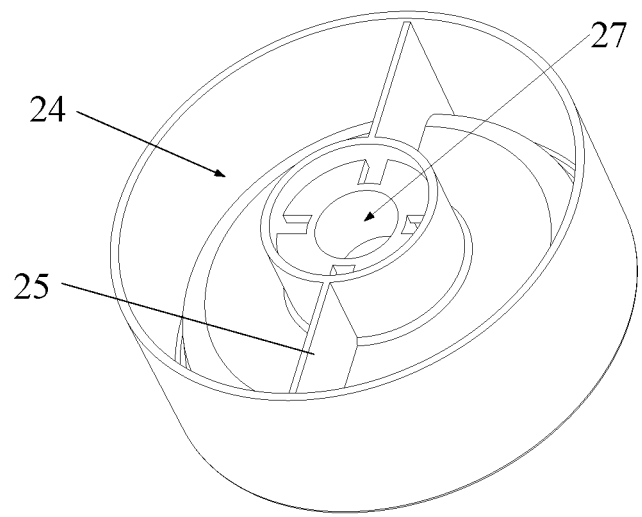
FIG. 11b illustrates another diagram of fragrance container according to an exemplary embodiment.

In some embodiments, as shown, for example, in FIGS. 11a and 11b, the fragrance compartment or container 20 includes a plurality of substantially separate chambers 24. A user can place a particular fragrance into each of the plurality of chambers 24, thus allowing the release of a compound scent. The user can choose his/her favorite fragrances for mixing and matching to produce a compound scent or to concoct a customized scent that has never existed before. In one embodiment, the chambers 24 in the fragrance compartment or container 20 are in communication with each other to enable the scents from a variety of fragrances to be mixed in the fragrance compartment or container 20 and then volatilized from the fragrance compartment or container 20. In an alternate embodiment, the plurality of chambers 24 are separate from one another, and the scents from a variety of fragrances are volatilized first, and then are mixed in the air outside the fragrance compartment or container 20. As shown in FIGS. 11a and 11b, in some embodiments, partitions 25 are provided in the fragrance compartment or container 20 to divide the fragrance compartment or container 20 into a plurality of chambers 24. For example, three or four partitions 25 can divide the fragrance compartment or container 20 into three chambers 24. In one embodiment, the compartment body 21 is formed by splicing a plurality of sub-compartments; each sub-compartment can be used individually, or a plurality of sub-compartments can form a complete compartment body 21. One sub-compartment forms one chamber 24, and a plurality of sub-compartments form a plurality of chambers 24. A user can place a variety of fragrances into the plurality of chambers 24, respectively, such that the electronic scent producing imitation candle device can release a compound scent.

In some embodiments, the electronic scent producing imitation candle device further comprises a WIFI (WIreless-FIdelity) controller and a WIFI receiver. Specifically, the WIFI controller is used to control the operations (or the state) of the electronic scent producing imitation candle device. The WIFI receiver receives a wireless signal, and converts the received wireless signal to an electric signal for input into the WIFI controller. The WIFI receiver is connected to a wireless network, and a mobile terminal is connected into the wireless network. An application software (APP) is downloaded to the mobile terminal that allows the mobile terminal to send out instructions to the WIFI receiver. The WIFI receiver receives the instructions, converts the instructions into an electric signal, and sends the electric signal to the WIFI controller. The WIFI controller controls, according to the electric signal, an operation of the electronic scent producing imitation candle device. The operation can includes turning the candle device on/off, setting the timer, etc. At the same time, the APP on the mobile terminal can display the state of the electronic scent producing imitation candle device. Examples of the mobile terminal include a cell phone, a tablet computer, or a laptop computer.

In some embodiments, as shown, for example, in FIGS. 5 through 8 and 10a through 10c, the base plate of the fragrance compartment or container 20 is depressed into the fragrance compartment or container 20 to form a recess 26 which increases the contact area between the base plate and the fragrance material. As a result, the heating element 30 thoroughly heats the fragrance. If the fragrance is wax or in solid form, the fragrance material is rapidly melted and is fully, evenly and rapidly volatilized into the air. As shown, for example in FIGS. 5 through 7, the cross-sectional shape of the base plate can be M-shaped. Since the heat transfer efficiency of a concave or convex contact surface is higher than the heat transfer efficiency of a flat contact surface, the heating element 30 thoroughly heats the fragrance.

Figure 5:
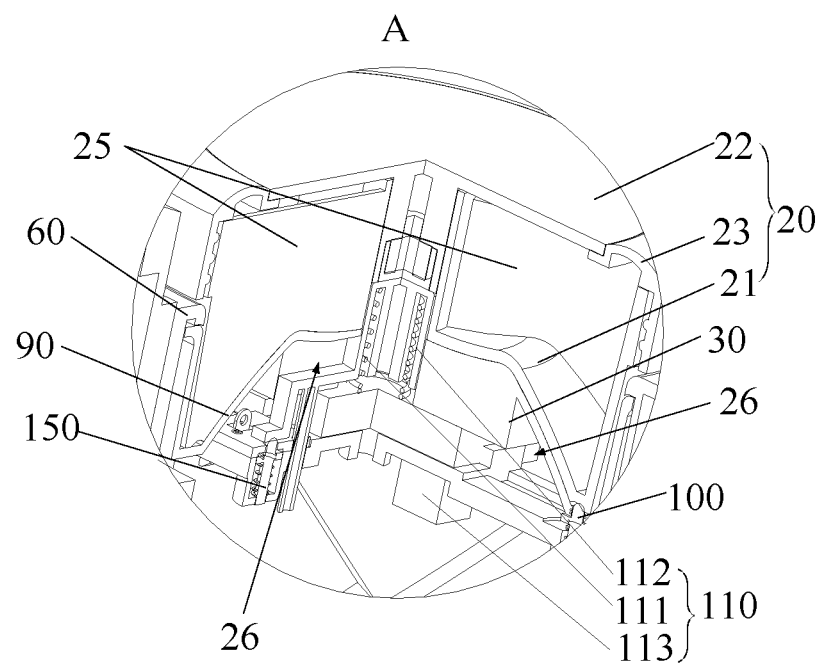
FIG. 5 is an enlarged view of section identified as region A in FIG. 4.
Figure 6:
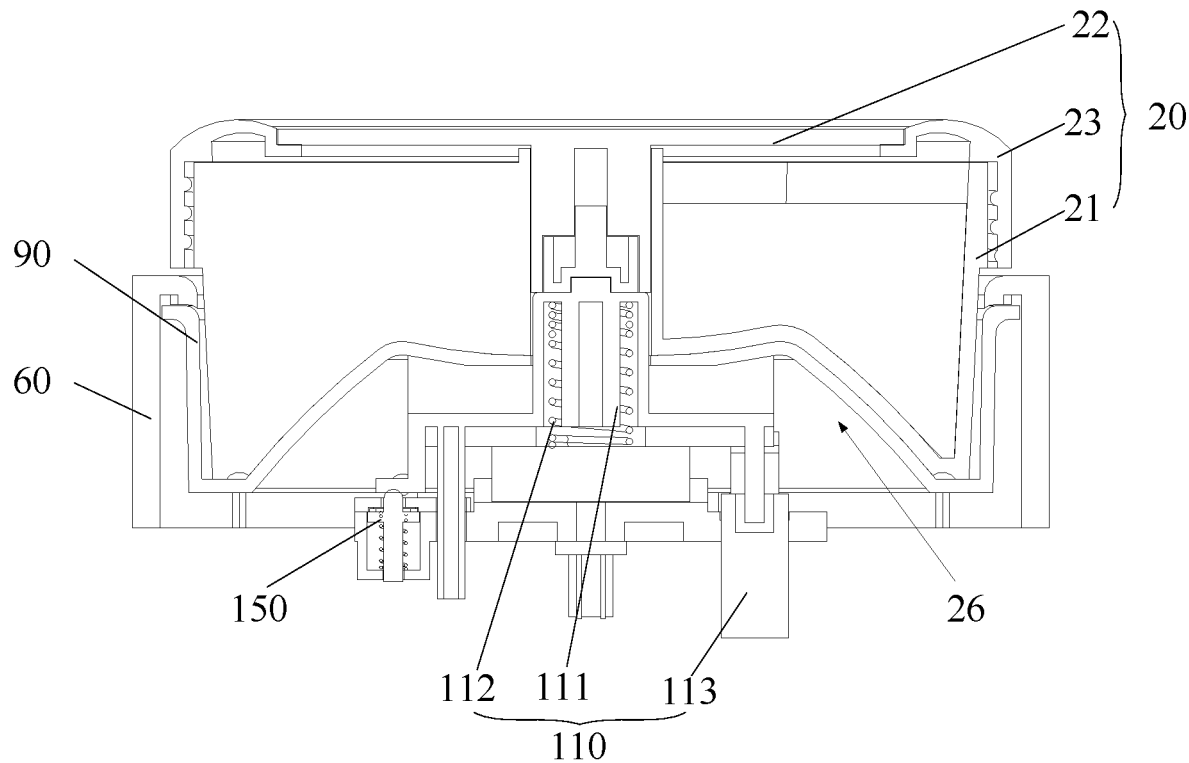
FIG. 6 illustrates some components of an electronic scent producing imitation candle device when the box lid of the fragrance container is in a closed position according to an exemplary embodiment.

In some embodiments, the electronic scent producing imitation candle device further comprises a thermally conductive member 90 (see, e.g., FIG. 5). The thermally conductive member 90 is disposed on the base plate, and the heating element 30 is disposed on the thermally conductive member 90. The heat of the heating element 30 is transferred to the thermally conductive member 90, and then the heat of the thermally conductive member 90 is further transferred to the base plate to heat the fragrance in the fragrance compartment or container 20. Since the thermally conductive member 90 is a good heat conductor, the heat quickly spreads to all parts of the thermally conductive member 90 and is distributed evenly thereon. The thermally conductive member 90 in turn heats the fragrance compartment or container 20 such that the base plate, and thus the fragrance material, are both evenly heated. The thermally conductive member 90 also increases the contact area between the heating element 30 and the base plate, which causes the fragrance compartment or container 20 to be heated more efficiently.

In some embodiments, as shown, for example, in FIGS. 5, 7, 10a and 10c, the electronic scent producing imitation candle device further comprises a protection device 100. The protection device 100 is constructed to shut down the power supply to the heating element 30 when the fragrance in the fragrance compartment or container 20 is below a nominal amount. If no fragrance is added to the fragrance compartment or container 20, the protection device 100 places the power supply to the heating element 30 in an off state, making a user unable to turn on the electronic scent producing imitation candle device. Additionally, during operation, when the fragrance in the fragrance compartment or container 20 is evaporated, in embodiments of the present application, a small amount of fragrance may still remain in the container (see, e.g., FIG. 10c). Under this condition, the protection device 100 also shuts down the power supply to the heating element 30. In this way, dry heating of the electronic scent producing imitation candle device is avoided, thereby improving the service life of the product. When there is little or no fragrance in the fragrance compartment or container 20, dry heating of the container can raise the temperature of the container and cause injuries or burns. Thus, by triggering the protection device 100 to the shut off the supply to the heating element 30, such burns or injuries are further avoided.

Figure 7:
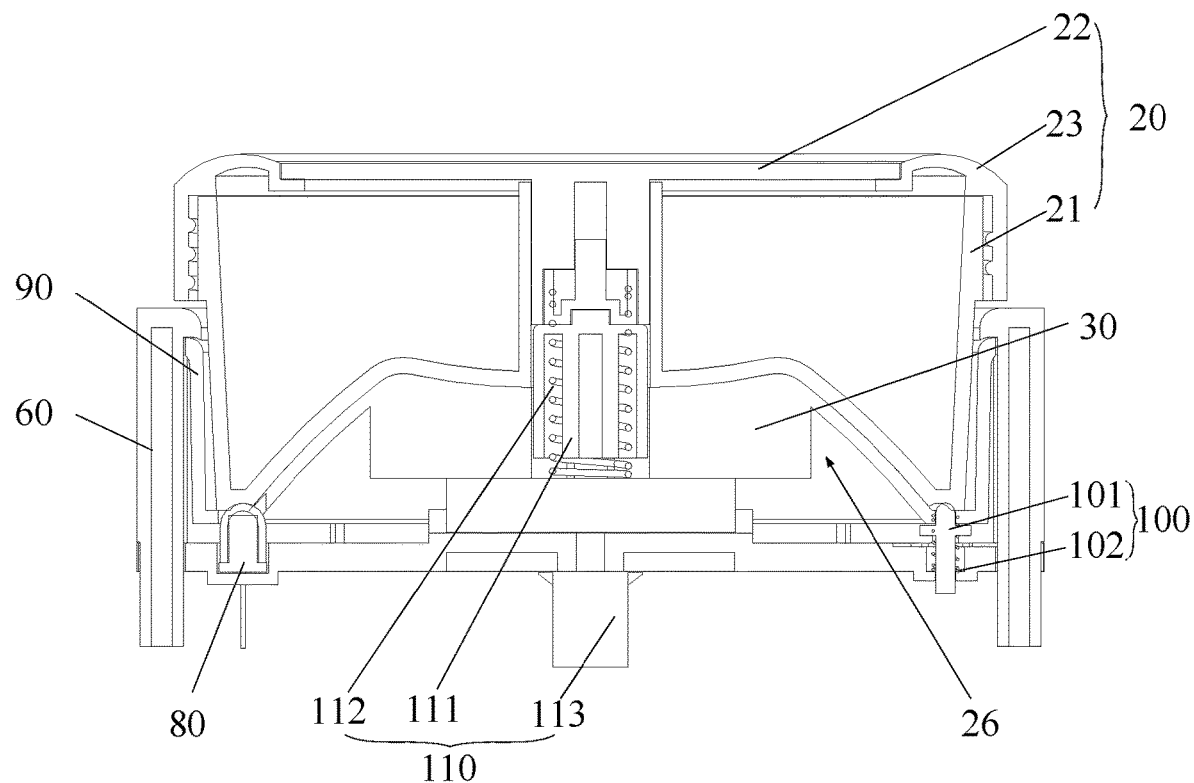
FIG. 7 illustrates further components of an electronic scent producing imitation candle device when the box lid of the fragrance container is in a closed position according to an exemplary embodiment.
Figure 8:
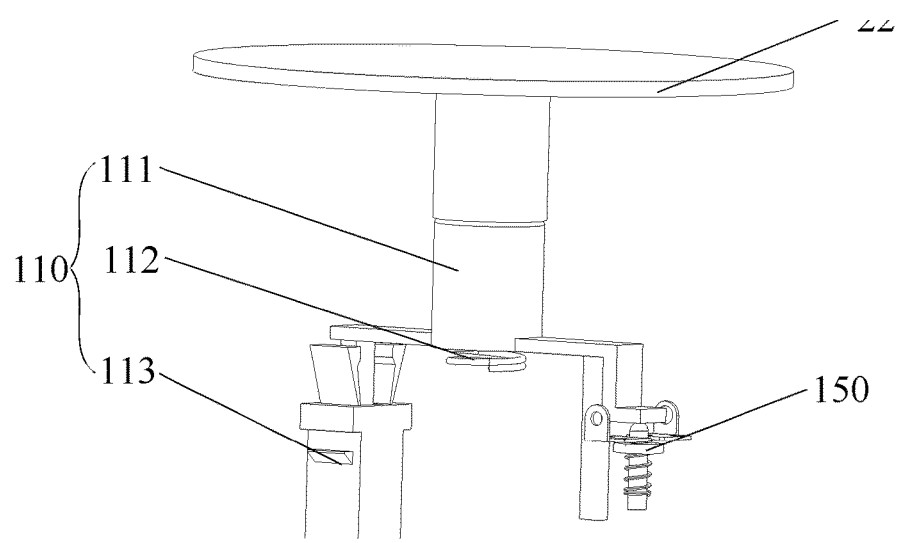
FIG. 8 illustrates a partial diagram of the box lid in a closed position according to an exemplary embodiment.
Figure 9:
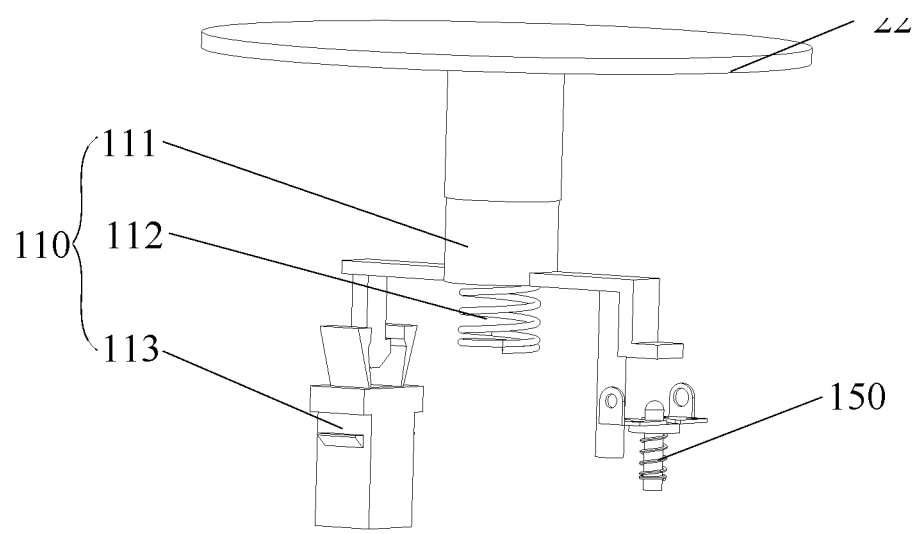
FIG. 9 illustrates a partial diagram of the box lid in an open position according to an exemplary embodiment.
Figure 10A:
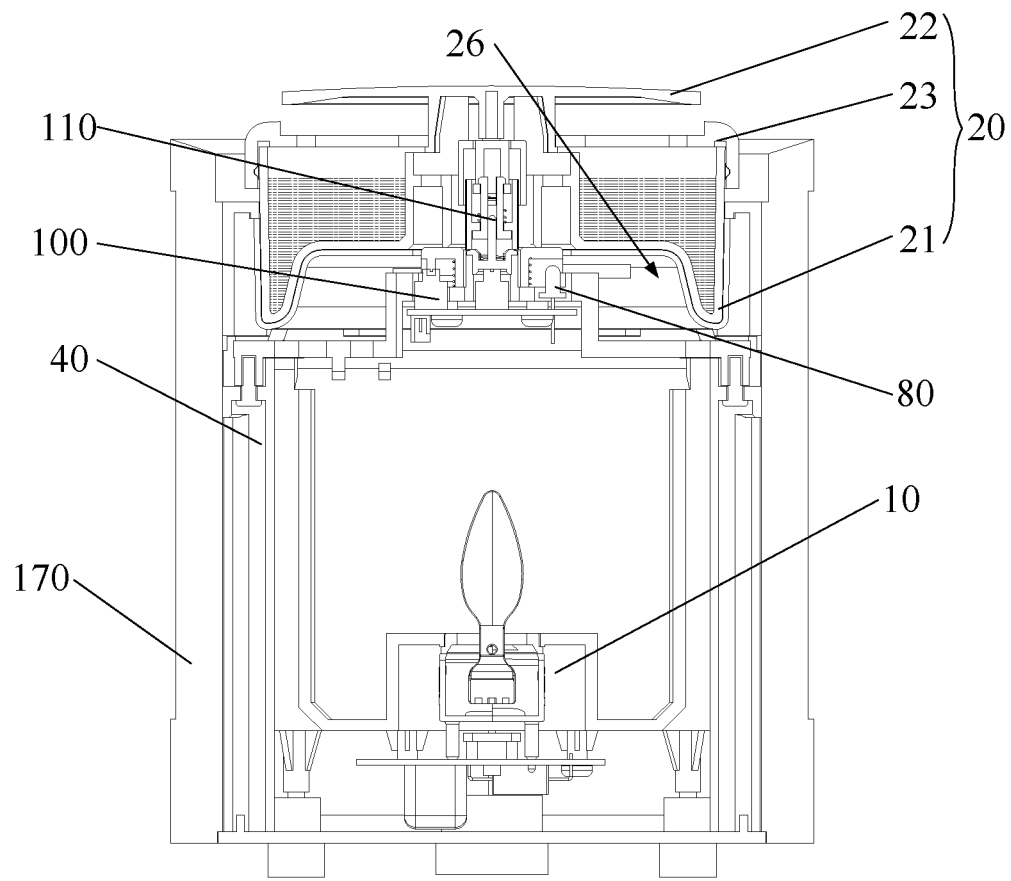
FIG. 10a illustrates a cross-sectional view of an electronic scent producing imitation candle device showing the box lid in an open position.
Figure 10B:
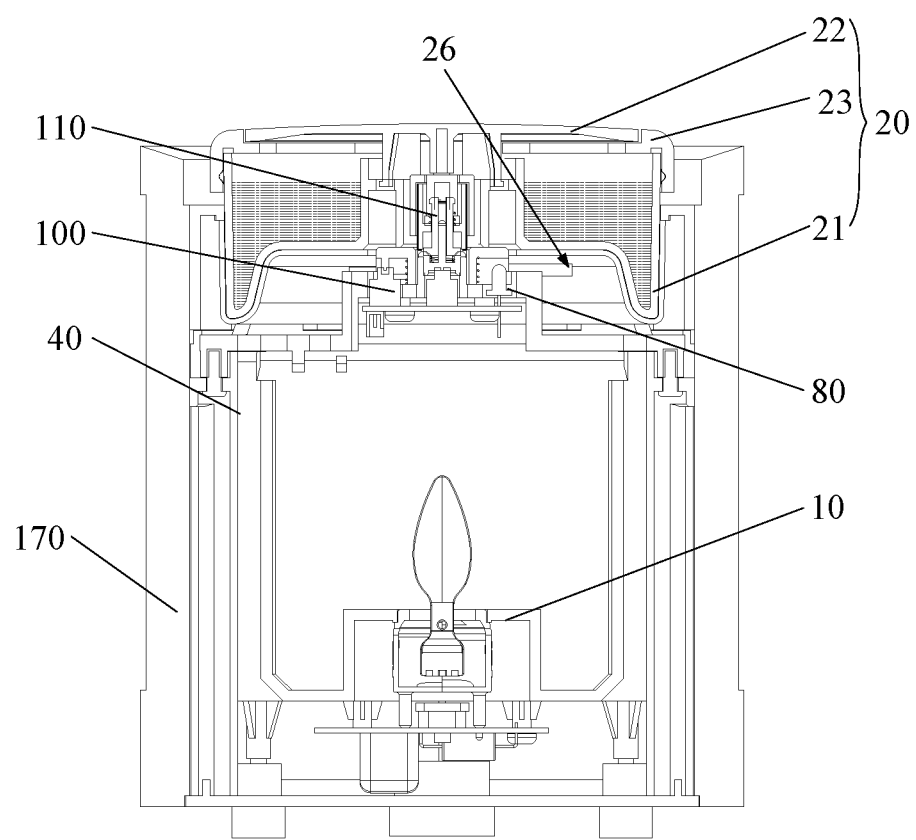
FIG. 10b illustrates a cross-sectional view of an electronic scent producing imitation candle device showing the box lid in a closed position.
Figure 10C:
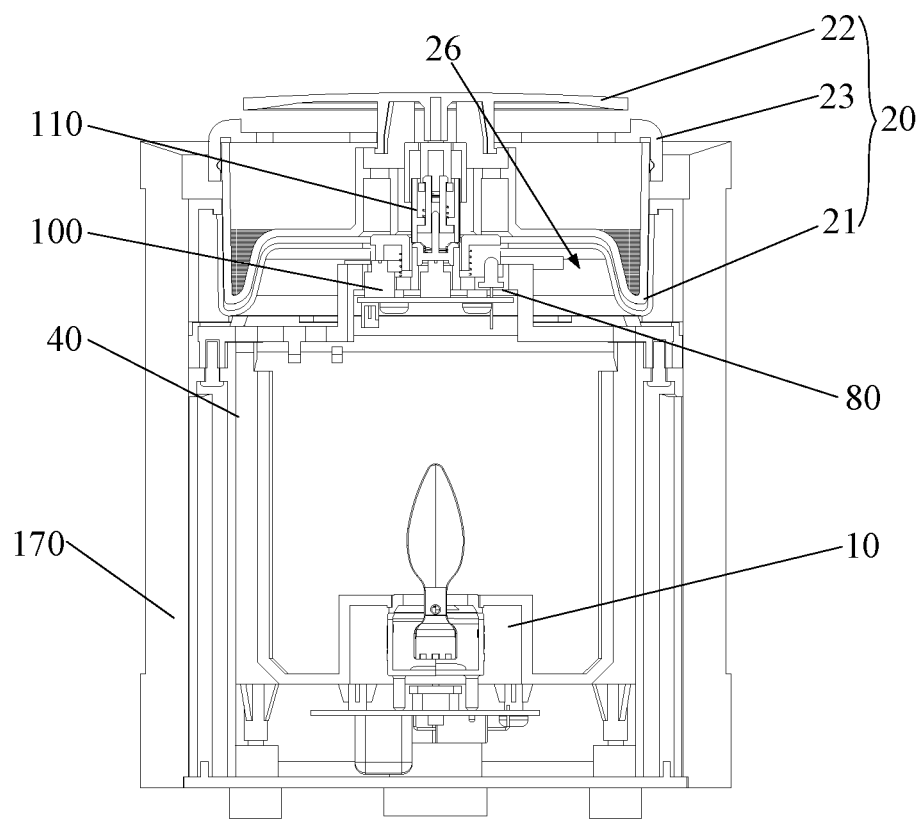
FIG. 10c illustrates a cross-sectional view of another electronic scent producing imitation candle device showing the box lid in an open position and a relatively small amount of fragrance remaining in the fragrance compartment.

In some embodiments, as shown, for example, in FIG. 7, the protection device 100 comprises a contact element 101 and a reset element 102. One end of the contact element 101 presses against the fragrance compartment or container 20, and the other end thereof is connected to a conductive switch that is connected to a power supply circuit of the heating element 30. The contact element 101 can move relative to the support assembly 40. The reset element 102 is disposed between the contact element 101 and the support assembly 40. When the fragrance in the fragrance compartment or container 20 is below a nominal amount, the reset element 102 drives the contact element 101 to open the conductive switch and shut down the power supply to the heating element 30. In particular, when there is no fragrance in the fragrance compartment or container 20, the conductive switch is in the closed state, and the heating element 30 cannot be powered on. When a fragrance is added in the fragrance compartment or container 20, the weight of the fragrance compartment or container 20 increases, and the fragrance compartment or container 20 presses on the contact device 101. The contact element 101 moves downward relative to the shell to trigger the conductive switch, such that the conductive switch is on and the heating element 30 is powered on to heat the fragrance compartment or container 20. In contrast, when the fragrance is evaporated, the weight of the fragrance compartment or container 20 gradually decreases, the pressure on the top plate decreases, and the top plate moves upward under the action of the reset element 102. When the fragrance in the fragrance compartment or container 20 is substantially fully evaporated, the contact element 101 drives to shut down the conductive switch, and the heating element 30 cannot be powered on. As noted earlier, when no fragrance is added in the fragrance compartment or container 20 (or when the fragrance is almost fully used), the protection device 100 shuts down the power supply to the heating element 30, such that a user is unable to turn on the electronic scent producing imitation candle device. The reset element 102 includes, but is not limited to, a spring for controlling the reset of the contact device 101. The contact element 101 includes, but is not limited to, a spring pin.

In some embodiments, as shown, for example, in FIGS. 5 through 10c, the electronic scent producing imitation candle device further comprises an elevation device 110 disposed on the support assembly 40 to control the compartment lid 22 and to open and cover the compartment body 21. Having such a device in place, avoids misplacement or loss of the compartment lid 22, which in turn causes the fragrance to volatilize naturally and prevents a foreign matter to fall into the fragrance.

In some embodiments, as shown, for example, in FIGS. 5 through 9, the elevation device 110 comprises an elevation bracket 111, an elastic element 112 and a locking base 113. The elevation bracket 111 is connected to the compartment lid 22 and movably installed onto the support 42. The elastic element 112 is disposed between the elevation device 110 and the support assembly 40; the locking base 113 is capable of being locked with, or disengaged from, the elevation bracket 111 and the compartment body 21 includes a through hole 27 running therethrough (see, e.g., FIG. 11a). One end of the elevation bracket 111 is positioned to run through the through hole 27 and connect to the compartment lid 22. When the compartment lid 22 is to be opened, the elevation bracket 111 is disengaged from the locking base 113, and the elastic element 112 drives the elevation bracket 111 to move and open the compartment lid 22 exposing the fragrance material inside the compartment body 21. When the compartment lid 22 is pressed down, the elevation bracket 111 is locked with the locking base 113, and the compartment lid 22 covers the compartment body 21. During use of the electronic scent producing imitation candle device, the compartment lid 22 covers the compartment body 21, and the fragrance compartment or container 20 is in a sealed state. When a user presses on the compartment lid 22, the elevation bracket 111 is disengaged from the locking base 113, the elevation bracket 111 moves upward under the action of the elastic element 112, and the compartment lid 22 is opened, allowing the fragrance in the fragrance compartment or container 20 to be volatilized into air. The compartment lid 22 can be pressed to move downward until it covers the compartment body 21, causing the elevation bracket 111 to also move downward under the action of the compartment lid 22 until it is locked with the locking base 113. As a result, the fragrance compartment or container 20 is in a sealed state. In such a way, the fragrance compartment or container 20 is opened only when it is used. At the same time, natural evaporation of the fragrance material in the fragrance compartment or container 20 is prevented when the fragrance device is not in use, thereby improving the service life of the fragrance. The elastic element 112 may include a spring for controlling the elevation device 111. Moreover, the locking base 113 may be, for example, in the form of a lock switch.

In some embodiments, as shown, for example, in FIGS. 5 through 9, the electronic scent producing imitation candle device comprises a power supply switch 150. The power supply switch 150 is connected to a circuit for delivering power to the heating element 30 and is controlled at least in part by the movement of the elevation bracket 111. In particular, when the compartment lid 22 opens the compartment body 21, the power supply switch 150 is activated to supply power to the heating element 30. When the compartment lid 22 is closed to cover the compartment body 21, the power supply switch 150 is deactivated, and the power to the heating element 30 is turned off. In operation, the compartment lid 22 may initially cover the compartment body 21 and the fragrance compartment or container 20 is in a sealed state. A user may subsequently press on the compartment lid 22, causing the elevation device 111 to be disengaged from the locking base 113. The elevation bracket 111 moves upward under the action of the elastic element 112, and at the same time, the power supply switch 150 is activated, connecting the heating element 30 to the power supply circuit and causing the heating element 30 to turn on. When the user presses on the compartment lid 22, it moves downward until it covers the compartment body 21; the elevation bracket 111 also moves downward under the action of the compartment lid 22 until it is engaged and locked with the locking base 113. At the same time, the elevation bracket 111 deactivates the power supply switch 150 to shut down the power supply to the heating element 30. In this state, the fragrance compartment or container 20 is in a sealed state, and the heating element 30 cannot generate heat. One of the benefits provided by these features is that it prevents or mitigates damage to the device, and possible fires and explosions that may ensue, when the user forgets to turn off heating element or the power supply. In particular, the safety risk associated with "dry heating" of the heating element 30 is mitigated, while providing an energy efficient and environmentally friendly scented candle device. It should be further noted that while the compartment lid 22, in some embodiments provides a complete seal for the compartment body 21, in other embodiment, the compartment lid 22 can only loosely cover the compartment body 21 to prevent contaminants from falling into the compartment body 21.

In some embodiments, as shown, for example, in FIG. 3*b*, the elevation bracket 111 projects beyond the top surface of the support assembly 40 and resembled a candle wick. For example, the elevation bracket 111 that projects beyond the support assembly 40 is has a dark color (e.g., black). When the fragrance compartment or container 20 is not installed, the end of the elevation bracket provides an appearance that the electronic scent producing imitation candle device is a real candle, thus enhancing the aesthetic quality of the product.

In some embodiments, the elevation device 110 comprises a magnet and an electric magnet. The magnet is disposed on the compartment lid 22; the electric magnet is disposed on the support assembly 40; when the electric magnet is powered on, it produces a force to repel the magnet such that the compartment lid 22 of the compartment body 21 is opened. During use of the electronic scent producing imitation candle device, the compartment lid 22 covers the compartment body 21, and the fragrance compartment or container 20 is in a sealed state. When the electric magnet is powered on, it produces a magnetic field that repels the magnetic field of the magnet. The magnet drives the compartment lid 22 to move upward under the action of the magnetic field repulsion force, the compartment lid 22 is opened, and the fragrance in the fragrance compartment or container 20 can be volatilized into the air. When the electric magnet is powered off, the magnetic field disappears, the compartment lid 22 and the magnet move downward under the action of gravity until the compartment lid 22 covers the compartment body 21, and the fragrance compartment or container 20 returns to a sealed state. In this way, the fragrance compartment or container 20 is opened only when it is in use. In some embodiments, the power supply switch 150 can also be applied to the elevation device 110. Such an implementation is particularly useful to remedy the situation in which the user forgets to open the compartment lid 22 while the heating element 30 is operating. In such a situation, the fragrance remains heated and under increasing pressure inside the scent compartment without being volatilized, thus creating a fire hazard and potentially causing burns or injuries to the user.

In some embodiments, the electronic scent producing imitation candle device further comprises a temperature control device (not shown) to control the on/off operation of the heating element 30 according to the fragrance temperature. The human skin has a certain heat tolerance, and a person will not burn if the temperature of the fragrance material and the container are kept at a "safe temperature." According to the disclosed embodiments, the safe temperature can be provided to, and implemented as part of, the scented candle device. During the operation of the electronic scent producing imitation candle device, the temperature control device detects the fragrance temperature (or the temperature of the fragrance compartment or container 20). When the fragrance temperature is higher than the above noted safe temperature, the temperature control device cuts off the power to the heating element 30, thus ensuring that the fragrance temperature does not exceed the safe temperature. When the fragrance temperature decreases to a lower temperature than the set temperature, the temperature control device turns on the power supply to the heating element 30, causing the heating element 30 to heat the fragrance and increase the volatility of the fragrance. As a result, the fragrance can be continuously and quickly volatilized into the air. In a specific embodiment, when the fragrance temperature is higher than 50° C. or 60° C., the temperature control device cuts off the power supply to the heating element 30. When the fragrance temperature is lower than 40° C., the temperature control device turns on the power supply to the heating element 30, which in turn causes the heating element 30 to heat the fragrance.

In some embodiments, the electronic scent producing imitation candle device further comprises a control device (not shown) to control the operations of the of the heating element 30 according to preset data. In some scenarios, different quantities of fragrance may be added to the fragrance compartment or container 20 in different venues or according to different user preferences. If a single heating method is used to heat the fragrance compartment or container 20, a relatively small quantity of fragrance can be quickly heated to release a scent, while it can take a relatively long time to fully heat a large quantity of the fragrance so that the scent is released. Moreover, in embodiments of the present technology, the fragrance may be in a variety of forms, such as in a block form, particle form, a liquid form, in a sticky (e.g., gel) form, and so on. As a result, each from of the fragrance material may require a different heating time. Therefore, it is beneficial to have the ability to set different heating modes according to the fragrance form and quantity. For example, a user may choose a particular heating mode according to the specific form and weight of a fragrance to, for example, ensure that the fragrance can be fully heated within 40 minutes. In some embodiments, the control device may be provided with the following modes: large volume mode, medium volume mode, and small volume mode, and according to the weight of a fragrance. The control device may be further provided with the following modes: block mode, particle mode, powder mode, liquid mode, and according to the shape of a fragrance so as to ensure that the fragrance is fully heated within a particular time.

Figure 12:
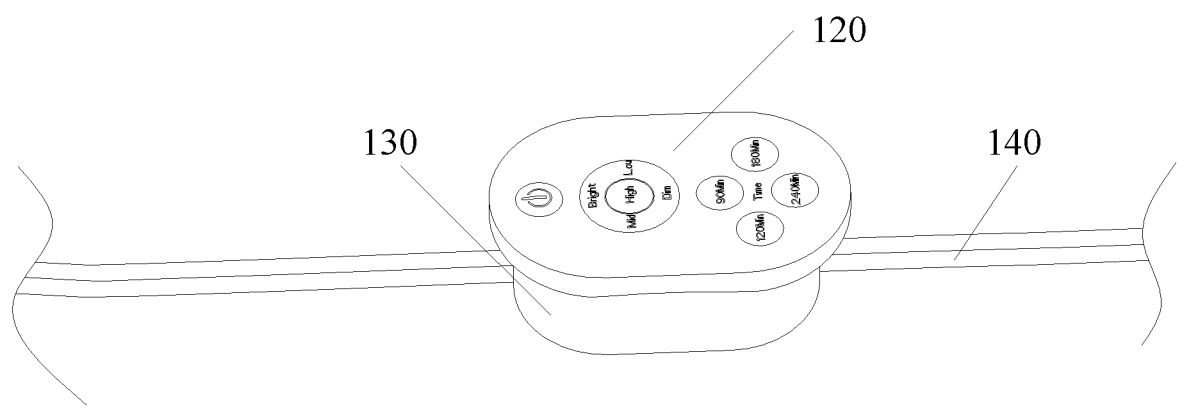
FIG. 12 illustrates a remote control positioned on a control panel according to an exemplary embodiment.
Figure 13:
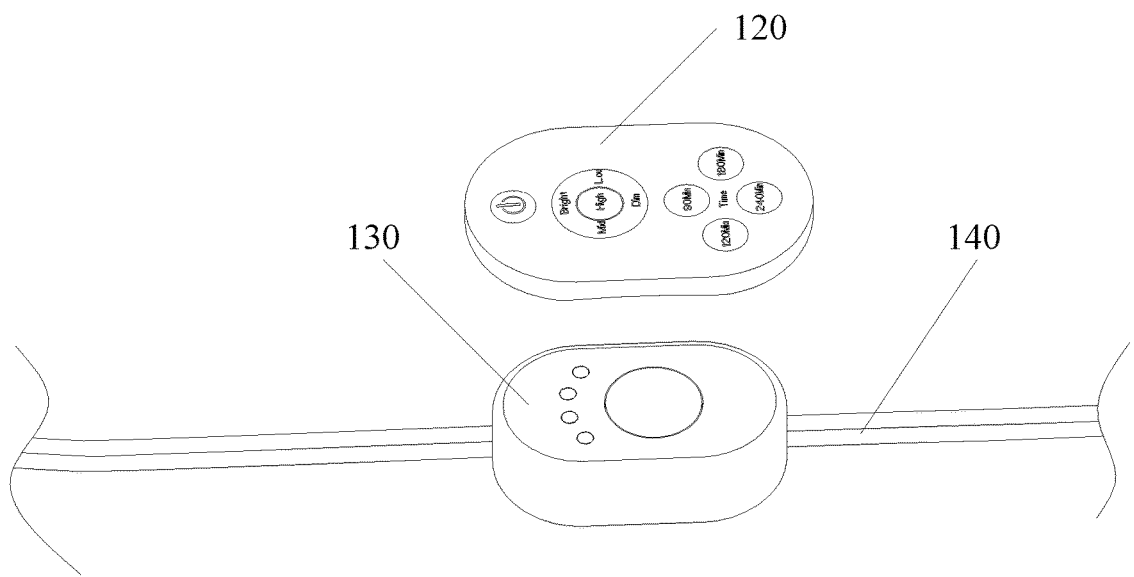
FIG. 13 illustrates an exploded view of the structure shown in FIG. 12.
Figure 14:
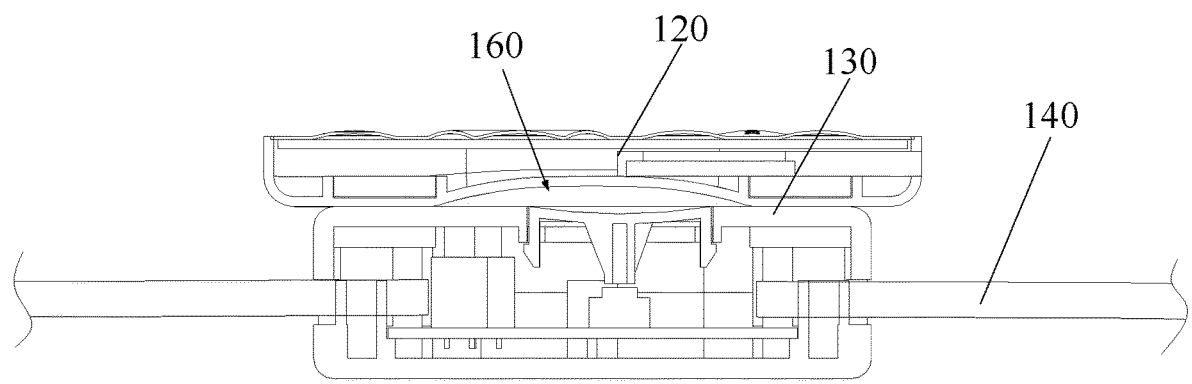
FIG. 14 illustrates a cross-sectional view of the structure shown in FIG. 12.

In some embodiments, as shown, for example, in FIGS. 12 through 14, the electronic scent producing imitation candle device further comprises a remote control 120. The remote control 120 is removably attached to a power cord 140 of the electronic scent producing imitation candle device. Typically, a switch of the electronic scent producing imitation candle device is disposed on the bottom of the shell. In such configurations, when the operating mode of the electronic scent producing imitation candle device needs to be selected (e.g., turned on, turned off, or adjusted), it becomes necessary to lift the electronic scent producing imitation candle device in order to change the setting of the switch that is positioned on the bottom of the device. Since the fragrance contained in the fragrance compartment or container 20 is easy to spill, it is beneficial to control the on/off and operating modes of the electronic scent producing imitation candle device without a need to lift the electronic scent producing imitation candle device. The remote control 120 remedies this issue and allows the user to change the operating modes of the device without a need to lift the candle device. According to the disclosed embodiments, when the use of the remote control 120 is completed, the user can attach the remote control 120 back onto the power cord 140, thus mitigating or reducing the possibility that the remote control 120 is misplaced or lost.

In some embodiments, the remote control 120 comprises a remote control body and an attachment bracket that is positioned on the power cord 140. The remote control body can be attached on the attachment bracket so as to position the remote control 120 on the power cord 140. The attachment bracket is shaped to enable the remote control 120 to have a relatively high contact area with the power cord 140 to allow the remote control 120 to be firmly affixed on the power cord 140 so that the probability that the remote control 120 falls off from the power cord 140 is reduced. In some embodiments, the remote control 120 includes a recess to allow the power cord 140 to be snapped into the remote control 120. The snap connection enables convenient and quick installation of the remote control 120 onto the power cord 140. The mode remote control 120 may, for example, use an infrared, Bluetooth, high-frequency module, and other wireless transmission modes.

In some embodiments, as shown, for example, in FIGS. 12 through 14, the power supply may also be provided with a control panel 130 that controls the on/off and operation modes of the electronic scent producing imitation candle device. The control panel 130 includes a magnet thereon, and the remote control 120 is also provided with a magnet thereon. This way, the remote control 120 can be attached to the control panel 130 via the attractive forces of the magnets. The user can easily remove the remote control 120 and replace it back onto the magnet on the cord when after use. In some embodiments, as shown, for example, in FIG. 14, the remote control 120 includes a clearance groove 160 to prevent the remote control 120 from contacting the buttons on the control panel 130 when the remote control 120 is attached to the control panel 130. The buttons on the control panel control operations of the electronic scented candle device. The remote control 120 and the control panel 130 are provided with mutually matching structures to enable a precise installation of the remote control 120 onto the control panel 130.

In some embodiments, the electronic scent producing imitation candle device further comprises an inclination sensor (not shown). The inclination sensor is constructed to shut down the power supplied to the heating element 30 when the electronic scent producing imitation candle device is tilted to a predetermined angle. When the electronic scent producing imitation candle device is inclined or inverted, the heated fragrance can flow out of the fragrance compartment or container 20 and into a circuit on the heating element 30 or onto other parts of the electronic scent producing imitation candle device. By cutting off the power supply, the electronic components are not short-circuited, thereby improving the safety of the product in use. In one embodiment, an inclination angle threshold can be set at, for example, an angle of 45°, 75° or another angle that is formed between the longitudinal axis of the electronic scent producing imitation candle device and the vertical axis. When the device is tilted to such an angle as sensed by the inclination sensor, the power supply is turned off. For example, three inclination sensors can be positioned in a triangle formation such that the angle therebetween is 45° or 75°, which ensures that, when the longitudinal axis of the electronic scent producing imitation candle device forms an angle of 45° or 75° relative to the vertical axis, the power supply to the heating element 30 is shut down. In some embodiments, the inclination sensors can include rolling ball switches.

In some embodiments, the electronic scent producing imitation candle device further comprises a voice control device (not shown) that controls that operating modes of the electronic scent producing imitation candle device based on input voice. The electronic scent producing imitation candle device also comprises a sensor element to receive an external input and convert the received external input to an electric signal to the control circuit. The external input may be an action of a user, such as voice, blowing the air, and blowing the air with a fan. For example, when a user makes an action of "blowing out" or "using a fan to extinguish" a simulated flame. The electronic scent producing imitation candle device can immediately capture this signal and produce a corresponding response, such as to cause the simulated flame to be extinguished, or the change the flickering. Additionally, or alternatively, when a user utters a corresponding instruction, the electronic scent producing imitation candle device can immediately capture this signal, process the signal to recognize the uttered words, and produce a corresponding response, such as to ignite, extinguish or change the flickering rate of the simulated candle.

In some embodiments, the electronic scent producing imitation candle device further comprises an atomization device (not shown) to produce a smoke-like to simulate a candle smoke of a "burning" flame, or the smoke of a candle when the candle is extinguished, thereby better simulating a real flame candle. In an example of the operation, when the sensor element or the voice control device detects an action of "blowing out", "using a fan to extinguish", or "shutting down." The sensor element or the voice control device sends a signal to the control circuit and the control circuit controls, according to the signal, the atomization device to produce a smoke mimicking a candle that has been extinguished. Moreover, when the smoke produced atomization device can heighten the atmosphere can be accompanied by a scent and enhance the aesthetic and aromatic appeal of the surroundings.

In some embodiments, the electronic scent producing imitation candle device may be used as a heating or warming device. For example, the fragrance compartment or container 20 can be removed, an article to be heated or warmed up, such as wine, is placed above the heating device where the fragrance compartment or container 20 is normally placed, thus enabling a user to enjoy warm wine under the candle light.

Figure 4:
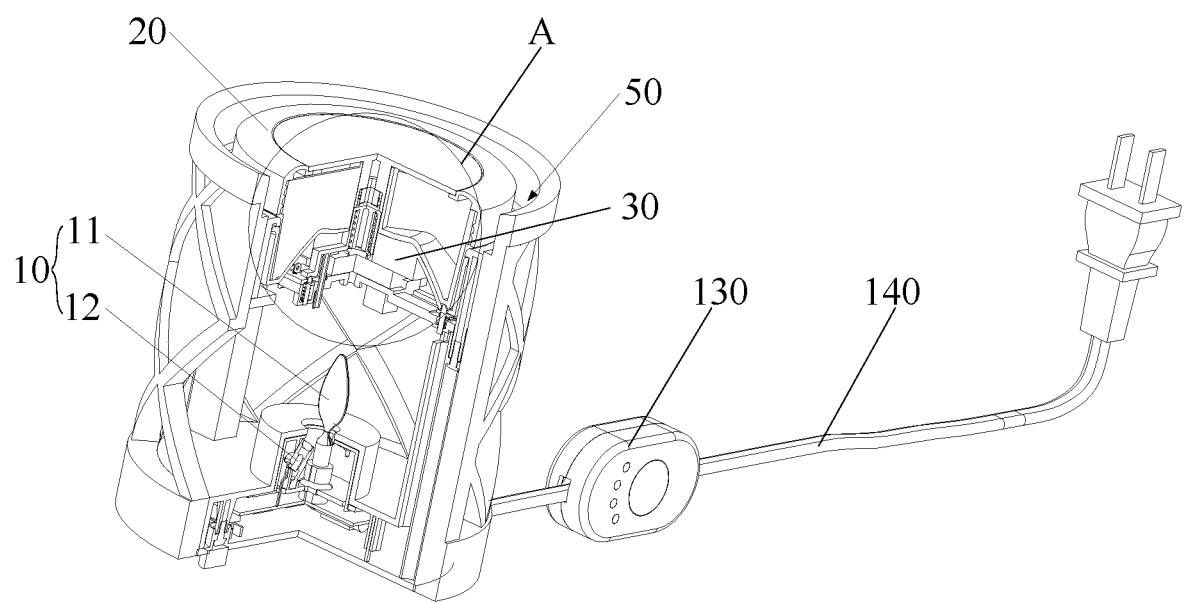
FIG. 4 illustrates a cross-sectional view of the electronic scent producing imitation candle device shown in FIG. 3.

In some embodiments, as shown, for example, in FIG. 4, the flame simulation device 10 comprises a light-emitting or light-reflecting section 11 and a light source 12. The upper portion of the light-emitting or light-reflecting section 11 is preferably formed to resemble a flame shape, and in some embodiments, it can make irregular movements. When a light emanates or illuminates the light-emitting or light-reflecting section 11, it can simulate an effect of a real flame that is moving. The light-emitting or light-reflecting section 11 includes a black-colored section to simulate a real candle wick after burning. The upper portion of the light-emitting or light-reflecting section 11 is preferably in the shape of a sheet-like flame, may be formed by combined two or more sheet-like flames, or may even be have a 3-dimensional shape. In some embodiments, the light-emitting or light-reflecting section 11 may be made of plastic or an organic synthetic material. In a preferred embodiment, the light-emitting or light-reflecting section 11 is made of a translucent material, such that the flame can be seen from both sides of the flame piece. In another preferred embodiment, the flame piece on the upper portion of the light-emitting or light-reflecting section 11 has an uneven thickness, preferably thin at the top and thick at the bottom. The flame piece may also be made to be thin at the top, thick in the middle, and thin at the bottom, to simulate light effects of a flame at different heights and improve the lifelikeness of the flame. In one embodiment, the lower portion of the light-emitting or light-reflecting section 11 includes a magnet or a magnetic material, such that the light-emitting element can make nonlinear movements that vary with time under the action of the magnetic field.

The device further comprises a power supply. In one example, a battery compartment is provided that accommodates one or more dry cells or rechargeable batteries. In the case of a rechargeable battery, in a preferred embodiment, the battery is charged in a wired charging mode. In other embodiments, the power supply may be charged in a wireless charging mode, with solar energy (e.g., captured solar energy is converted into electrical energy for storage when the product is not in use). In another embodiment, as shown, for example, in FIG. 2, the power supply may include a plug is directly connected to an AC outlet. In one embodiment, the base 41 of the support assembly 40 includes a removable screw or buckle. A user may take off the screw, then replace the battery or replace the battery with a power cord 140, thus allowing the user to switch the power supply according to his/her own needs. It should be noted that a single device may be powered via more than one of the above noted mechanisms.

In some embodiments, the electronic scent producing imitation candle device further comprises a proximity sensor that can detect the present of a human near the device. When the proximity sensor detects that there is a person near the electronic scent producing imitation candle device, it automatically starts the operation of the electronic scent producing imitation candle device. When the presence of a human is not detected, the electronic scent producing imitation candle device automatically shuts down. The detection range of the proximity sensor in one exemplary configuration is 0-10 meters. Moreover, the detection region can be fan-shaped or can include a plurality of fan shapes. In one embodiment, the proximity sensor device operates based on the microwave Doppler principle, and uses a planar antenna as the sensing mechanism. In particular, when a wave of a certain frequency meets an obstacle, part of the wave is reflected. If the obstacle is stationary, the wavelength of the reflected wave is constant. If the obstacle is moving toward the source of the wave, the wavelength of the reflected wave is shorter than the wavelength of the original wave; if the obstacle is moving away from the wave source, the wavelength of the reflected wave is longer than the wavelength of the original wave. This way, through the use of a microwave source and reception of the reflected waves, the movement of the surrounding objects can be determined. The disclosed proximity sensor device in one example transmits and receives signals at a microwave frequency of 10.525 GHz. By receiving the microwave signals, converting them into electrical signals, and analyzing the electrical signals, the device can determine if a person is in the vicinity of the electronic scent producing imitation candle device. For instance, the proximity sensor can compare the amplitude and width of the electric signals to improve the detection accuracy of the detection. In another embodiment, the human sensing device may be additionally, or alternatively, performed the detection in an infrared mode by detecting the infrared (heat) radiation released by the human body. The sensor can include lenses, photosensitive elements, photosensitive circuits, and mechanical components. Regardless of whether a human body is moving or stationary, the photosensitive element can always produce a voltage difference, and the photosensitive circuit can produce an identification signal to indicate the presence of a person.

In some embodiments, the electronic scent producing imitation candle device further comprises a light sensing device to control the on/off state of the electronic scent producing imitation candle device in accordance with light intensity. When the light sensing device is activated and the environment lighting is dimmed to a degree, the light sensing device controls the electronic scent producing imitation candle device to start its operations. For example, the device is turned on, and the intensity of the light source 12 can be controlled according to the sensed ambient light intensity. Further, when the intensity of the ambient light exceeds a predetermined level, the light sensing device can control the electronic scent producing imitation candle device to stop its operation. For example, the device can be turned off.

In some embodiments, the electronic scent producing imitation candle device further comprises a pressure sensor and a control device. The pressure sensor that is used to detect and/or measure when a pressure is applied to the electronic scent producing imitation candle device, such as when the device is touched. The detected pressure is then converted to electric signal for input into the control device. A user may control the operations of the electronic scent producing imitation candle device by, for example, touching the electronic scent producing imitation candle device. Specifically, the user can touch the shell 170 that includes the pressure sensor; the pressure sensor converts the pressure applied by the user to an electric signal, the control device receives the electric signal and controls an operation of the electronic scent producing imitation candle device, such as to turn the device on or off, to set or activate a timer, and the like. For example, the device can be configured such that one touch of the shell 170 by the user turns the device on, one more touch of the shell 170 turns the device off, continuous touches of the shell 170 activate a timer, and detection of a pressure for a predetermined length of time activates an operational mode of the device. In some example implementations, the control device comprises CPU 1 and CPU 2. When a person touches the sensor, or approaches the sensor area (in case of a proximity sensing, or capacitive touch sensing), the pressure sensor senses (e.g., via detecting a changed in capacitance), and transmits a pulse signal to an input pin of CPU 1. CPU 1 can be configured to perform signal conditioning (e.g., filtering out noise) transmit a low level to the main control CPU 2. The main control CPU 2 can control, according to the low level from CPU 1, the operations of the electronic scent producing imitation candle device.

In some embodiments, the electronic scent producing imitation candle device includes a display to display time, operational mode and duration of an operation to inform a user regarding the operations and status of the device. In some embodiments, the electronic scent producing imitation candle device includes a wireless module that can communicate with a remote device. The user can use the remote device (e.g., via using a software application on the remote device) to control the operations of the electronic scent producing imitation candle device. In some embodiments, the electronic scent producing imitation candle device If the user leaves home and forgets to turn off the electronic scent producing imitation candle device can be configured as a networked device (e.g., having Internet of Things (IoT) features and capabilities), which allows a user to control the operations of the device from practically any remote location. For example, the user can turn the device off from another location when the user is outside of his/her house. Similarly, the user can remotely turn the device on prior to returning home in order to refresh the air inside the house when the user reaches his/her home.

In some embodiments, the disclosed imitation candle device can be adapted to operate as an electronic candle that may be used for ceremonial or worship purposes. For example, the device can include a holding container that can be used to hold an ancestor's ashes, and a photo of the ancestor for attachment to the holding container. As such, the electronic flame assembly can be used as a simple urn. In some cemeteries, power plugs are provided. A user can place the electronic flame assembly at a cemetery to operate as an eternal flame and as a device to hold ashes. For example, the holding container can be a sealed container, which prevents moisture and other contaminants from entering the holding container to damage articles therein.

Other applications of the disclosed device can include using the holding container to grow plants. For example, the top section of the device may be used for growing plants, while the bottom portion may be used to provide an imitation flame.

In one embodiment, the bottom of the support assembly includes an attachment structure that allows the electronic flame assembly to be attached to a horizontal fixture. In particular, the attachment structure can include a threaded hole that can be screwed onto a threaded pole that is positioned horizontally. The attachment structure may also be an attachment buckle that can snap onto an attachment slot that is positioned horizontally.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. An electronic imitation candle device, comprising:
a shell;
a flame element positioned in the shell to simulate a real flame;
a fragrance compartment positioned in the shell;
a heating element positioned below the fragrance compartment to provide heat to the fragrance compartment; and
a protection device comprising a contact pin, a spring, and a conductive switch, wherein the protection device is positioned under the fragrance compartment, wherein the spring is positioned to surround the contact pin,
wherein one end the contact pin is coupled to the fragrance compartment to detect a presence or absence of a fragrance material within the fragrance compartment;
wherein another end of the contact pin is coupled to the conductive switch, which is coupled to the heating element to affect a supply of power to the heating element in response to detection of the presence or absence of the fragrance material;
wherein upon detection of an empty fragrance compartment or a presence of a nominal amount of fragrance in the fragrance compartment the spring is configured to drive the contact pin to open the conductive switch and shut down the electronic imitation candle device; and
wherein upon detection of a presence of fragrance compartment beyond the nominal amount the spring is configured to drive the contact pin to close the conductive switch and turn on the electronic imitation candle device.

2. The electronic imitation candle device of claim 1, wherein the flame element is disposed at a distance from the heating element to form a gap configured to allow heat dissipation for the heating element.

3. The electronic imitation candle device of claim 1, comprising additional one or more flame elements within the shell.

4. The electronic imitation candle device of claim 1, comprising additional one or more heating elements positioned below the fragrance compartment.

5. The electronic imitation candle device of claim 1, wherein the fragrance compartment includes one or more partitions that divide the fragrance compartment into a plurality of chambers.

6. The electronic imitation candle device of claim 5, wherein each chamber is configured to hold a fragrance material that is different from fragrance materials in other chambers.

7. The electronic imitation candle device of claim 5, wherein the plurality of chambers is in communication with each other to enable scents from a variety of fragrances to be mixed in the fragrance compartment.

8. The electronic imitation candle device of claim 1, comprising:

an insulation layer disposed between the heating element and the shell to prevent overheating of the shell.

9. The electronic imitation candle device of claim 1, wherein the fragrance compartment includes a compartment lid that is removably positioned on top of the fragrance compartment to cover the fragrance compartment.

10. The electronic imitation candle device of claim 9, wherein the fragrance compartment includes an insulation lid positioned under the compartment lid to impede heat transfer to the compartment lid.

11. The electronic imitation candle device of claim 9, wherein the compartment lid comprises a hollow structure that protrudes downward from a center of the fragrance compartment, the hollow structure including an elastic material therein that allows the compartment lid to be pressed downward or to be moved upward.

12. The electronic imitation candle device of claim 11, further comprising a locking base positioned below the fragrance compartment to lock the compartment lid in place.

13. The electronic imitation candle device of claim 11, further comprising an elevation device configured to control an opening of the compartment lid, wherein the elevation device comprises the elastic material.

14. The electronic imitation candle device of claim 1, comprising:
a support assembly within the shell, the support assembly comprising a base and a top plate, wherein the fragrance compartment is positioned above the top plate.

15. The electronic imitation candle device of claim 14, wherein the spring is disposed between the contact pin and the support assembly.

16. The electronic imitation candle device of claim 14, wherein the top plate of the support assembly includes an installation groove for accommodating a placement of the fragrance compartment inside the installation groove.

17. The electronic imitation candle device of claim 1, wherein the shell comprises an observation window thereon to allow the flame element to be viewed from outside of the electronic imitation candle device.

18. The electronic imitation candle device of claim 1, wherein the protection device is configured to activate or deactivate in response to a weight of the fragrance compartment.

19. The electronic imitation candle device of claim 1, further comprising a temperature control device to control an operation of the heating element according to a temperature of a fragrance material inside the fragrance compartment.

20. The electronic imitation candle device of claim 1, further comprising a remote-control device configured to control an operation of the electronic scent producing imitation candle device from a remote location.

* * * * *